United States Patent
Arjona Antolín et al.

(10) Patent No.: US 9,475,741 B2
(45) Date of Patent: Oct. 25, 2016

(54) METHOD FOR OBTAINING HIGHER ALCOHOLS

(71) Applicant: Abengoa Bioenergía Nuevas Technolgías, S. A., Seville (ES)

(72) Inventors: Ricardo Arjona Antolín, Seville (ES); Juan Luís Sanz Yagüe, Seville (ES); Avelino Corma Canós, Valencia (ES); Marcelo Eduardo Domine, Valencia (ES); Fernando Vidal Barrero, Seville (ES); Francisco Antonio Ladrón de Guevara Vidal, Seville (ES)

(73) Assignee: ABENGOA BIOENERGÍA NUEVAS TECHNOLOGÍAS, S. A., Sevilla (ES)

( * ) Notice: Subject to any disclaimer, the term of this patent is extended or adjusted under 35 U.S.C. 154(b) by 0 days.

(21) Appl. No.: 14/411,752

(22) PCT Filed: Jul. 1, 2013

(86) PCT No.: PCT/ES2013/070448
§ 371 (c)(1),
(2) Date: Dec. 29, 2014

(87) PCT Pub. No.: WO2014/001597
PCT Pub. Date: Jan. 3, 2014

(65) Prior Publication Data
US 2015/0166443 A1  Jun. 18, 2015

(30) Foreign Application Priority Data
Jun. 29, 2012 (EP) .................................. 12382261

(51) Int. Cl.
| | | |
|---|---|---|
| *C07C 29/32* | (2006.01) |
| *B01J 25/00* | (2006.01) |
| *B01J 23/00* | (2006.01) |
| *B01J 23/62* | (2006.01) |
| *B01J 23/656* | (2006.01) |
| *B01J 23/89* | (2006.01) |
| *C07C 29/34* | (2006.01) |

(52) U.S. Cl.
CPC .............. *C07C 29/32* (2013.01); *B01J 23/007* (2013.01); *B01J 23/62* (2013.01); *B01J 23/656* (2013.01); *B01J 23/6562* (2013.01); *B01J 23/89* (2013.01); *B01J 23/896* (2013.01); *B01J 25/00* (2013.01); *C07C 29/34* (2013.01); *B01J 2523/00* (2013.01)

(58) Field of Classification Search
CPC ............................... C07C 29/34; C07C 29/32
See application file for complete search history.

(56) References Cited

U.S. PATENT DOCUMENTS

2014/0179958 A1* 6/2014 Zhang ..................... C07C 29/34
568/905

FOREIGN PATENT DOCUMENTS

| WO | WO00/38832 | 7/2000 |
| WO | WO2009/026510 | 2/2009 |
| WO | WO2014/001597 | 1/2014 |

OTHER PUBLICATIONS

International Search Report dated Nov. 11, 2013 issued in PCT/ES2013/070448.

\* cited by examiner

*Primary Examiner* — Jafar Parsa
(74) *Attorney, Agent, or Firm* — Polsinelli PC

(57) ABSTRACT

The invention relates to a method for obtaining higher alcohols from lower alcohols with a catalyst that is a metal oxide comprising gallium and a noble metal selected from the list containing Pd, Pt, Ru, Rh and Re.

23 Claims, 3 Drawing Sheets

METHOD FOR OBTAINING HIGHER ALCOHOLS

The present invention relates to the obtainment of higher alcohols by using a metal-oxide-type catalyst that comprises gallium and a noble metal. Therefore, the present invention belongs to the field of catalytic processes for obtaining higher alcohols.

BACKGROUND OF THE INVENTION

The synthesis of high-molecular-weight alcohols (containing between 4 and 8 carbon atoms) from low-molecular-weight alcohols (e.g. methanol and ethanol) has acquired considerable interest in recent years due to the potential use of these oxygenated compounds in the preparation of automotive fuels and also additives for the latter.

In particular, n-butanol (n-ButOH), with a worldwide production of approx. 4-5 million tons per year, is primarily used as an additive for liquid fuels, as a starting chemical reagent in the plastics industry and also as an extraction agent in the aroma and fragrance industry. N-butanol is primarily produced through the petrochemical pathway. Methods for producing n-butanol by fermentation are also widely known.

Alternatively, n-butanol can be obtained by means of the well-known Guerbet reaction, which makes it possible to convert a low-molecular-weight alcohol (e.g. ethanol) into a linear or branched alcohol with a higher molecular weight in the presence of a metal alkoxide dissolved in the alcohol to be transformed. The main disadvantages associated with the Guerbet reaction are: i) the production of water, which must be eliminated from the reaction medium in order to favour the formation of the desired compounds, ii) the production of carboxylic acids, and iii) the use of homogeneous catalysts, which cause both corrosion in the reactors and final separation problems.

U.S. Pat. No. 5,300,695 discloses K, Na, Ba and Cs cations exchanged zeolites, amongst others, as catalysts in the condensation of low-molecular-weight alcohols, to obtain selectivities to iso-butanol of 30%-35% at a 45% methanol conversion rate. Several basic oxides containing Cu, commonly used in the production of high-molecular-weight alcohols from syn-gas ($CO/H_2$), have also been assayed in methanol and ethanol condensation reactions, to produce high-molecular-weight alcohols, albeit with a relatively low production of $C_4$ alcohols (U.S. Pat. No. 5,387,570). Another group of catalysts used are calcium-phosphate-based materials of the hydroxyapatite type (US20070255079). These catalysts have been tested in fixed-bed continuous reactors at 300° C. with very short contact times. The best results were obtained for materials with a Ca/P molar ratio of 1.5-1.7, with ethanol conversion of 12% and selectivities to $C_4$ alcohols (primarily iso-butanol) close to 78%. Oxides of alkaline-earth metals, particularly materials based on MgO with supported transition metals, have also been used for the transformation of ethanol into n-butanol.

In recent years, numerous scientific publications and patents have appeared on the use of hydrotalcite-type materials as catalysts in alcohol condensation reactions, such as the Guerbet reaction, in both batch systems and fixed-bed continuous reactors. The studies performed with these mixed Mg—Al oxides revealed that the catalytic activity of these materials is dependent on the nature, density and strength of the basic surface sites, which, in turn, are dependent on the molar Mg/Al composition in the solid. For example, international application WO2009026510 discloses a process for synthesising n-butanol by means of a material derived from the thermal decomposition of a hydrotalcite which preferably comprises magnesium and aluminum. Moreover, WO2009097312, US20100160693 and WO2009097310 disclose materials obtained by the thermal decomposition of hydrotalcites modified by the inclusion of metal carbonates and ethylenediamine-tetraacetates, which have been developed by DU PONT as catalysts in alcohol condensation reactions operating in a fixed bed at 300° C. and atmospheric pressure. The best results under these conditions have been achieved with a material derived from Mg—Al-based hydrotalcite (containing $OH^-$ as the anion), which presents high ethanol conversion (≈44%) with moderate selectivities (≈44%) to n-butanol. When these same materials were assayed in the catalytic conversion of ethanol into n-butanol in the presence of hydrogen in the reaction system, the yields of n-butanol obtained were significantly lower in all cases.

Given the importance of higher alcohols, new, improved catalysts are still needed for the synthesis thereof.

DESCRIPTION OF THE INVENTION

The present invention relates to a process for obtaining higher alcohols in the presence of a catalyst that is a metal oxide which comprises gallium.

The invention presents the following advantages with respect to the catalysts in the state of the art:
  at a given concentration of palladium, the hydrotalcite-derived catalysts that comprise gallium in their structure provide higher yields of n-butanol than their analogues without gallium,
  moreover, they also show a greater catalytic activity (measured through the TON, Turnover Number, parameter) than catalysts that present the same concentration of Pd but do not have gallium in their structure, which means that the catalysts are more stable under the reaction conditions, performing a greater number of catalytic cycles in a given reaction time,
  a lower temperature is required in order to perform the process.

Therefore, one aspect of the present invention relates to a process for obtaining (hereinafter process of the invention) $C_3$-$C_{15}$ higher alcohols, preferably between $C_3$-$C_8$, which comprises a contact step between at least one reagent selected from the list that comprises methanol, ethanol (EtOH), propanol and isopropanol, and a catalyst, where said catalyst is a metal oxide that comprises the following metals:
  M1 is at least one bivalent metal selected from the list that comprises Mg, Zn, Cu, Co, Mn, Fe, Ni and Ca,
  M2 is trivalent Ga,
  and, moreover, said catalyst contains a noble metal selected from the list that comprises Pd, Pt, Ru, Rh and Re, preferably Pd.

The term "$C_3$-$C_{15}$ higher alcohols" is understood to mean any linear or branched alkyl chain with at least one hydroxyl functional group which has between 3 and carbon atoms. Likewise, the term "$C_3$-$C_8$ higher alcohols" is understood to mean any linear or branched alkyl chain with at least one hydroxyl functional group which has between 3 and 8 carbon atoms. Thus, the higher alcohol will preferably be a $C_3$, $C_4$, $C_5$, $C_6$, $C_7$ or $C_8$. Non-limiting examples would be propanol, isopropanol, n-butanol, 2-butanol, 2-methyl-2-butanol, 3-methyl-1-butanol-1-pentanol, 2-pentanol, 3-pentanol, 2,2-dimethyl-1-propanol, 3-methyl-2-butanol, 1,5- pentanediol, 2,4-pentanediol, 2,2-dimethyl-1,3-propanediol, 1,2-butanediol, 1,3-butanediol, 1,4-butanediol, 2,3-butanediol, 1-heptanol, 2-heptanol, 3-heptanol, 4-heptanol, 2-methyl-2-hexanol, 2,2-dimethyl-3-pentanol-1-octanol, 2-octanol, 3-octanol, 4-octanol, 2-ethyl-1-hexanol, 3-ethyl-1-hexanol and 2,2-dimethyl-3-hexanol. Obviously, when the reagent is a $C_3$, the higher alcohol obtained will be at least a $C_4$, preferably a $C_4$, $C_5$, $C_6$, $C_7$ or $C_8$.

"Bivalent metal" or "trivalent metal" is understood to mean a metallic cation with a +2 or +3 charge, respectively.

In a preferred embodiment of the process of the invention, the catalyst is the metal oxide that further comprises an M3 metal, where M3 is at least one trivalent metal selected from the list that comprises Al, La, Fe, Cr, Mn, Co and Ni.

In a more preferred embodiment of the process of the invention, the metal oxide is obtained from the total or partial thermal decomposition of a hydrotalcite with formula $[M1_{1-(x+y)}M2_yM3_x(OH)_2][A^{m-}_{(x+y)/m}\cdot nH_2O]$, where M1, M2 and M3 have been described previously, A is at least one anion selected from the list that comprises hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II); x is a value between 0 and 0.5, preferably, x is a value between 0.1 and 0.5, and, even more preferably, between 0.1 and 0.4; y is a value between 0.00001 and 0.49, preferably between 0.00005 and 0.45, and, even more preferably, between 0.0001 and 0.4; m is an integer between 1 and 4; and n is greater than 0, preferably n is a value between 0 and 100, and, even more preferably, between 0 and 20. n indicates the number of crystallisation water molecules and is dependent on the composition of the hydrotalcite cations.

"Hydrotalcite" is understood to mean the structural family of laminar mixed hydroxides with the formula described above. The general structure of hydrotalcites is well-known to persons skilled in the art.

The term "thermal decomposition" is understood to mean a chemical decomposition or structural change caused by the action of heat. This decomposition may be total or partial, depending on whether said decomposition is performed to completion or, on the contrary, is partially performed. This thermal decomposition may be performed at temperatures greater than 150° C. and in the presence of an oxidising or a non-oxidising gas.

In a preferred embodiment of the process of the invention, the hydrotalcite is obtained by the co-precipitation of at least one M1 compound and at least one compound of a trivalent metal selected from the list that comprises M2 and M3; preferably, the hydrotalcite is obtained by the co-precipitation of M1, M2 and M3 compounds.

Preferably, the co-precipitation is performed in the aqueous phase. The co-precipitation of the compounds may be preferably performed following the addition of a solution of at least one anion A selected from the list that comprises hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one M1 compound and at least one compound of a trivalent metal selected from the list that comprises M2 and M3, preferably M1, M2 and M3 compounds. This anion A may be introduced between the sheets of the resulting hydrotalcite. In order to obtain solutions of anion A, sodium and/or potassium salts thereof may be used. Preferably, A is at least one anion selected from the list that comprises carbonate, bicarbonate and hydroxide. The best results are obtained when the co-precipitation is performed at a pH higher than 7, preferably between 10 and 14. Moreover, in order to regulate the pH, sodium and/or potassium hydroxide are preferably used.

Preferably, prior to the precipitation of said compounds, there is a dissolution of at least one M1 compound and at least one compound of a trivalent metal selected from the list that comprises M2 and M3, preferably M1, M2 and M3 compounds. Soluble M1, M2 and M3 compound is understood to mean any salt that, when in contact with a solvent, is dissociated, preferably a polar solvent, more preferably water. Examples of soluble M1, M2 and M3 compounds may be nitrates, halides, sulfates, carboxylates and, in general, oxoacids that comprise M1, M2 or M3; preferably, the soluble M1, M2 and M3 compounds are nitrates.

Another embodiment of the present invention is the process as described above, where M1 is Mg. Moreover, M3 is preferably Al. As regards the anion, A is preferably at least one anion selected from the list that comprises $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H_5COO^-$, and $SO_4^{2-}$; even more preferably, $CO_3^{2-}$, $HCO_3^-$, $O_2^-$ and $OH^-$.

Another embodiment of the present invention is the process as described above, where the thermal decomposition of hydrotalcite is performed by calcination, preferably by calcination in an atmosphere of oxygen, nitrogen or any mixture thereof. Preferably, the calcination is performed at a temperature ranging between 250° C. and 650° C., preferably between 350° C. and 550° C. The thermal decomposition of hydrotalcite is preferably performed for an interval of 0.5 to 48 hours, preferably between 1 and 24 hours. This process may be performed by heating the hydrotalcite in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

The gels resulting from the co-precipitation as described above are filtered, washed with water and adequately dried. The presence of a hydrotalcite-type structure may be corroborated by means of X-ray diffraction analysis (XRD), whilst the composition (quantity and type of constituent) of the hydrotalcite or the corresponding mixed oxide obtained by thermal decomposition of the aforementioned hydrotalcite may be determined by means of inductively coupled plasma mass spectrometry (ICP-MS) and chemical analysis, amongst others.

In another preferred embodiment of the process of the present invention, the noble metal is added to the metal oxide by wet impregnation, incipient volume impregnation or deposition-precipitation, even more preferably by incipient volume impregnation. The incipient volume impregnation method, also called incipient wetness impregnation method, is based on the use of a minimum quantity of liquid for the impregnation, only that which is necessary to reach the maximum saturation of the corresponding solid. The best yields of n-butanol have been obtained when the hydrotalcites containing Ga are impregnated with Pd.

Another embodiment of the present invention is the process as described above, where the concentration of the noble metal in the metal oxide ranges between 0.001% and 10% by weight with respect to the total metal oxide, preferably between 0.01% and 5%.

In a particular embodiment of the present invention, in the event that M2 has not been incorporated into the hydrotalcite in the co-precipitation step, M2 may be incorporated into the metal oxide in a step subsequent to the synthesis by means of wet impregnation, incipient volume impregnation and/or deposition-precipitation. This incorporation may be performed prior to or simultaneously with the addition of at least one noble metal selected from the list that comprises Pd, Pt, Ru and Rh, preferably Pd and Pt, and, even more preferably, Pd.

At a given concentration of palladium, the hydrotalcite-derived catalysts that comprise gallium in their structure provide higher yields of n-butanol in a nitrogen atmosphere than their analogues without gallium. Furthermore, they also show a higher TON than catalysts that present the same concentration of Pd but do not have gallium in their structure. This fact is an indication of the greater stability of the catalysts of the invention under the reaction conditions.

Moreover, as may be observed in FIGS. 1 and 2, the catalysts of the invention present higher selectivities to butanol at a given ethanol conversion than the catalysts in the state of the art.

In a preferred embodiment of the process of the invention, following the addition of the noble metal, there is a calcination step. This calcination is preferably calcination in an atmosphere of oxygen, nitrogen or any mixture thereof. This calcination is preferably performed at a temperature ranging between 250° C. and 650° C., and, even more preferably, between 350° C. and 550° C. This calcination is preferably performed for an interval ranging between 0.5 and 48 hours, preferably between 1 and 24 hours, and, even more preferably, between 1 and 6 hours. This process may be performed by heating the hydrotalcite in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In a preferred embodiment, the process of the invention further comprises a reduction step following calcination of the hydrotalcite. During the reduction, the noble metal, which acts as one of the main active sites in the process, is reduced. This reduction step is preferably performed in an $H_2$ atmosphere and, preferably, at a temperature ranging between 200° C. and 500° C., more preferably between 250° C. and 450° C. This reduction is preferably performed for an interval of between 0.5 and 48 hours, preferably between 1 and 24 hours, and, even more preferably, between 1 and 6 hours. Preferably, the reduction takes place immediately prior to the contact step with the reagent.

Another embodiment of the present invention is the process as described above, where the higher alcohol is a $C_4$, preferably n-butanol. Amongst other by-products, $C_3$-$C_{20}$ higher primary alcohols, preferably $C_4$-$C_{12}$, are also obtained in the process. Moreover, $C_3$-$C_{20}$ higher secondary alcohols, preferably $C_3$-$C_{11}$, may also be obtained. As discussed above, when the reagent is a $C_3$, the higher alcohol that will be obtained will be at least a $C_4$. The hydroxyl function of said higher secondary alcohols will be preferably located at the $C_2$. $C_2$-$C_6$ aldehydes may also be obtained. In particular, the main by-products are preferably ethanal, 2-butanol, butanal, 1-hexanol, 2-hexanol, hexanal, 1-octanol, 2-octanol and octanal.

In another preferred embodiment of the process of the invention, the reagent is ethanol, methanol or any mixture thereof, preferably ethanol.

In another preferred embodiment of the process of the invention, contact between the reagent and the catalyst is performed in a reactor selected from the list that comprises discontinuous reactor, continuous stirred-tank reactor, fixed-bed continuous reactor and fluidized-bed continuous reactor, preferably a discontinuous reactor.

In the particular embodiment wherein the reactor is a discontinuous reactor, contact between the reagent and the catalyst is performed at a temperature ranging between 50° C. and 450° C., preferably between 100° C. and 300° C. In this process, the weight ratio between the reagent and the catalyst is preferably between 2 and 200, preferably between 5 and 100. Moreover, it is performed for a time interval ranging between 2 minutes and 200 hours, preferably between 1 hour and 100 hours.

In another preferred embodiment of the process of the invention, contact between the reagent and the catalyst is performed at a pressure of up to 120 bars, preferably between 20 and 80 bars.

In another preferred embodiment of the process of the invention, contact between the reagent and the catalyst is performed in an atmosphere of nitrogen, argon, hydrogen or any mixture thereof, preferably in a nitrogen-hydrogen atmosphere. Usually, higher selectivities to n-butanol are obtained in the presence of hydrogen.

Another embodiment of the present invention is the process as described above, further comprising a step of separation of unreacted reagents from the obtained $C_3$-$C_{15}$ higher alcohols. Preferably, said unreacted reagents are recirculated to the contact step between reagents and catalyst, and more preferably, the unreacted reagent comprises ethanol. Even more preferably, the unreacted reagent is ethanol. Recirculation of unreacted reagents diminishes the waste production.

Another embodiment of the present invention is the process as described above, further comprising a step of separation of intermediates from the obtained $C_3$-$C_{15}$ higher alcohols. Preferably, said intermediates are recirculated to the contact step between reagents and catalyst. By the term "intermediate" in the context of the invention is meant any compound that it is formed from the reagents and that it can be later converted into $C_3$-$C_{15}$ higher alcohols. If it is not later converted into $C_3$-$C_{15}$ higher alcohols, the intermediate can also be called a by-product. Preferably by the term "intermediate" is meant aldehyde intermediates. More preferably, if the reagent is methanol, the intermediate aldehyde is methanal, if ethanol, is acetaldehyde (also called ethanal) and if propanol, propanal. More preferably, the intermediate comprises acetaldehyde. Even more preferably, the intermediate is acetaldehyde.

Acetaldehyde is formed as an intermediate in the dimerisation of ethanol as shown:

$$CH_3CH_2OH \rightarrow CH_3CHO + H_2 \qquad (1)$$

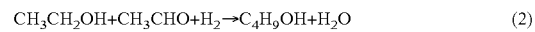

$$CH_3CH_2OH + CH_3CHO + H_2 \rightarrow C_4H_9OH + H_2O \qquad (2)$$

The global reaction is:

$$2CH_3CH_2OH \rightarrow C_4H_9OH + H_2O \qquad (3)$$

As shown in Example 19, the feeding of aldehyde intermediates to the contact step between reagents and catalyst not only increases the conversion but also the selectivity of $C_3$-$C_{15}$ higher alcohols.

Other intermediates or by-products could be obtained in the process of the invention, as listed above. In the separation step, the desired unreacted reagent and/or desired intermediate are separated from any of the rest of the products (by the term "products" here is meant any of the compounds that can be found after the contact between reagents and catalyst has taken place, and includes unreacted reagents, intermediates, by-products, $C_3$-$C_{15}$ higher alcohols, water and impurities present in the feed). However, a certain amount of products can be present in the recirculation feed.

Another embodiment of the present invention is the process as described above, further comprising the feeding of fresh acetaldehyde to the contact step between reagents and catalyst. In other words, acetaldehyde can be optionally recirculated and/or it can be fed from an external source. Preferably the acetaldehyde is obtained from the dehydration of ethanol. More preferably this process of dehydration of ethanol is carried out at the same time than the main process for obtaining $C_3$-$C_{15}$ higher alcohols.

Throughout the description and the claims, the word "comprises" and the variants thereof are not intended to exclude other technical characteristics, additives, components or steps. For persons skilled in the art, other objects, advantages and characteristics of the invention will arise partly from the description and partly from the practise of the invention. The following examples and figures are provided for illustrative purposes, and are not intended to limit the scope of the present invention.

EXAMPLES

Figure 1:
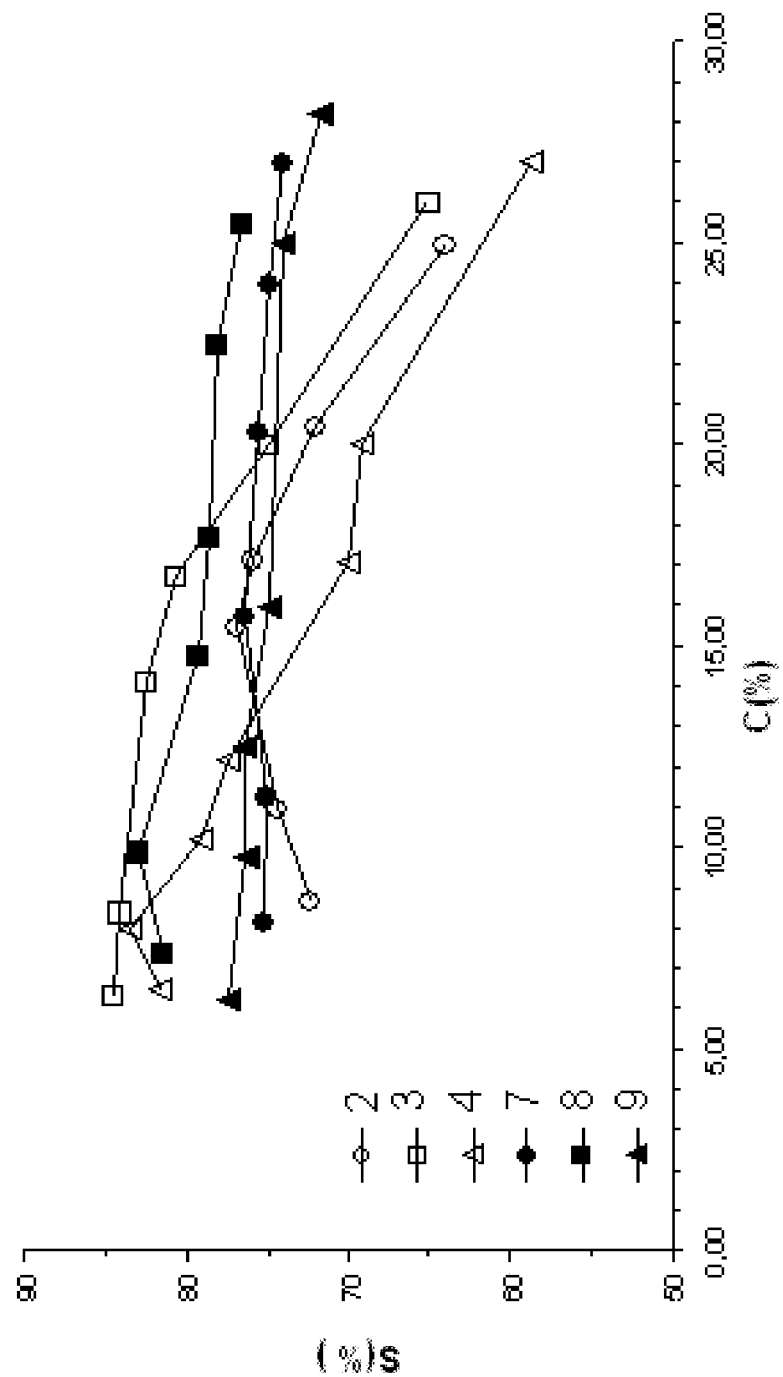
FIG. 1. Shows a comparative graph of the selectivities of the Pd/HT-4 and Pd/Ga-HT-4 catalysts in an $N_2$ atmosphere as a function of the conversion. S (%): Selectivity to butanol in mole %; C (%): ethanol conversion in mole %; 2: 1% Pd/HT-4 (Ex. 2); 3: 0.5% Pd/HT-4 (Ex. 3); 4; 0.25% Pd/HT-4 (Ex. 4); 7: 1% Pd/0.29% Ga-HT-4 (Ex. 7); 8: 0.50% Pd/0.29% Ga-HT-4 (Ex. 8); 9: 0.24% Pd/0.29% Ga-HT-4 (Ex. 9).

Below we will illustrate the invention by means of assays performed by the inventors, which demonstrate the efficacy in the obtainment of higher alcohols of the hydrotalcite-derived catalysts that comprise gallium in their structure.

Example 1

Synthesis of the HT-4 Catalyst (Mg/Al Molar Ratio≈4)

It was prepared by means of a standard co-precipitation process using two solutions. The first solution contained 36.45 g of $Mg(NO_3)_2.6H_2O$ and 13.60 g of $Al(NO_3)_3.9H_2O$, dissolved in 67.79 g of Milli-Q water, with a molar concentration of Al+Mg of 1.5. The second solution contained 12.53 g of NaOH and 16.16 g of $Na_2CO_3$ in 89.63 g of Milli-Q water, and was used to produce the adequate precipitation of the Al and Mg species, and to set the pH of the total mixture at ≈13. Both solutions were added, at a total flow velocity of 30 ml/h for approx. 4 h, to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 14-16 h, and a mixed oxide called HT-4 was obtained, with a Mg/Al molar ratio ≈3.8 and a surface area (BET method) of 257 $m^2$/g. The BET method refers to the Brunauer-Emmett-Teller isotherm method.

Example 2

Synthesis of the 1% Pd/HT-4 Catalyst

It was prepared from the material prepared as described in Example 1, wherein the incorporation of Pd (1.0% by weight, theoretical) into the HT-4 material was performed by means of the incipient wetness impregnation method, using, in this case, 0.030 g of $Pd(NH_3)_4Cl_2.6H_2O$ dissolved in 2.000 g of Milli-Q water, to impregnate 1.014 g of HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pd/HT-4 material, characterised by chemical analysis and ICP-MS, contained ≈1.00% by weight of Pd.

Example 3

Synthesis of the 0.5% Pd/HT-4 Catalyst

It was prepared from the material prepared as described in Example 1, wherein the incorporation of Pd (0.5% by weight, theoretical) into the HT-4 material was performed by means of the incipient wetness impregnation method, using, in this case, 0.015 g of $Pd(NH_3)_4Cl_2.6H_2O$ dissolved in 2.000 g of Milli-Q water, to impregnate 1.023 g of HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pd/HT-4 material, characterised by chemical analysis and ICP-MS, contained ≈0.50% by weight of Pd.

Example 4

Synthesis of the 0.25% Pd/HT-4 Catalyst

It was prepared from the material prepared as described in Example 1, wherein the incorporation of Pd (0.3% by weight, theoretical) into the HT-4 material was performed by means of the incipient wetness impregnation method, using, in this case, 0.008 g of $Pd(NH_3)_4Cl_2.6H_2O$ dissolved in 2.000 g of Milli-Q water, to impregnate 1.023 g of HT-4. Once impregnated, the solid obtained was dried in an oven at 100° C. for 14-16 h; thereafter, it was calcined in air at 450° C. for 3-4 h, and, subsequently, it was reduced at 350°

C. in an $H_2$ atmosphere for 3 h prior to the catalytic application thereof. The resulting Pd/HT-4 material, characterised by chemical analysis and ICP-MS, contained ≈0.25% by weight of Pd.

Example 5

Synthesis of the 0.80% Pt/HT-4 Catalyst

It was prepared from the HT-4 material prepared as described in Example 1, wherein the incorporation of Pt (1.0% by weight, theoretical) into the HT-4 material was performed by means of the incipient wetness impregnation method, using 0.025 g of $H_2Cl_6Pt.6H_2O$ dissolved in 2.000 g of Milli-Q water, to impregnate 1.025 g of HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pt/HT-4 material, characterised by chemical analysis and ICP-MS, contained ≈0.80% by weight of Pt.

Example 6

Synthesis of the 0.29% Ga-HT-4 Catalyst

It was prepared by means of a standard co-precipitation process using two solutions. The first solution contained 29.89 g of $Mg(NO_3)_2.6H_2O$, 10.90 g of $Al(NO_3)_3.9H_2O$ and 0.06 g of $Ga(NO_3)_3.9H_2O$, dissolved in 55.18 g of Milli-Q water, with a molar concentration of (Al+Mg+Ga) of 1.5. The second solution contained 12.52 g of NaOH and 10.52 g of $Na_2CO_3$ in 72.60 g of Milli-Q water, and was used to produce the adequate precipitation of the Mg, Al and Ga species, and to set the pH of the total mixture at ≈13. Both solutions were added, at a total flow velocity of 30 ml/h for approximately 4 h, to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 14-16 h. The hydrotalcite (Ga-HT-4) obtained was calcined in air at 450° C. for 3-4 h, to obtain a mixed oxide with a Mg/Al molar ratio ≈3.8, a Ga content of 0.29% by weight (measured by chemical analysis and ICP-MS), and a surface area (BET method) of 262 $m^2/g$.

Example 7

Synthesis of the 1% Pd/0.29% Ga-HT-4 Catalyst

It was prepared from the material prepared as described in Example 6, wherein the incorporation of Pd (1.0% by weight, theoretical) into the Ga-HT-4 material was performed by means of the incipient wetness impregnation method, using, in this case, 0.030 g of $Pd(NH_3)_4Cl_2.6H_2O$ dissolved in 1.700 g of Milli-Q water, to impregnate 1.100 g of 0.29% Ga-HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pd/0.29% Ga-HT-4 material, characterised by chemical analysis and ICP-MS, contained ≈1.00% by weight of Pd.

Example 8

Synthesis of the 0.50% Pd/0.29% Ga-HT-4 Catalyst

It was prepared from the material prepared as described in Example 6, wherein the incorporation of Pd (0.5% by weight, theoretical) into the Ga-HT-4 material was performed by means of the incipient wetness impregnation method, using, in this case, 0.016 g of $Pd(NH_3)_4Cl_2.6H_2O$ dissolved in 1.800 g of Milli-Q water, to impregnate 1.129 g of 0.29% Ga-HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pd/0.29% Ga-HT-4 material, characterised by chemical analysis and ICP-MS, contained ≈0.50% by weight of Pd.

Example 9

Synthesis of the 0.24% Pd/0.29% Ga-HT-4 Catalyst

It was prepared from the material prepared as described in Example 6, wherein the incorporation of Pd (0.3% by weight, theoretical) into the Ga-HT-4 material was performed by means of the incipient wetness impregnation method, using, in this case, 0.008 g of $Pd(NH_3)_4Cl_2.6H_2O$ dissolved in 1.800 g of Milli-Q water, to impregnate 1.011 g of 0.29% Ga-HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pd/0.29% Ga-HT-4 material, characterised by chemical analysis and ICP-MS, contained ≈0.24% by weight of Pd.

Example 10

Synthesis of the 1.06 Pt/0.29% Ga-HT-4 Catalyst

It was prepared from the material prepared as described in Example 6, wherein the incorporation of Pt (1.0% by weight, theoretical) into the Ga-HT-4 material was performed by means of the incipient wetness impregnation method, using, in this case, 0.045 g of $H_2Cl_6Pt.6H_2O$ dissolved in 1.700 g of Milli-Q water, to impregnate 1.003 g of Ga-HT-4. Once impregnated, the solid obtained was dried in an oven at 100° C. for 14-16 h; thereafter, it was calcined in air at 450° C. for 3-4 h, and, subsequently, it was reduced at 350° C. in an $H_2$ atmosphere for 3 h prior to the catalytic application thereof. The resulting Pt/0.29% Ga-HT-4 material, characterised by chemical analysis and ICP-MS, contained ≈1.06% by weight of Pt.

Example 11

Synthesis of the 0.74% Pd/0.48% Ga/HT-4 Catalyst

It was prepared from the HT-4 material prepared as described in Example 1, wherein the incorporation of Ga (0.7% by weight, theoretical) into the HT-4 material was performed by means of the incipient wetness impregnation method, using, in this case, 0.026 g of $Ga(NO_3)_3.9H_2O$ dissolved in 1.920 g of Milli-Q water, to impregnate 1.000 g of HT-4. Once impregnated, the solid obtained was dried in an oven at 100° C. for 14-16 h. The incorporation of Pd (1.0% by weight, theoretical) into the solid obtained was performed by means of the incipient wetness impregnation method, using, in this case, 0.095 g of Pd(NH$_3$)$_4$Cl$_2$.6H$_2$O dissolved in 1.400 g of Milli-Q water, to impregnate 1.540 g of the solid obtained in the first impregnation. Once impregnated, the final solid was dried in an oven at 100° C. for 14-16 h; thereafter, it was calcined in air at 450° C. for 3-4 h, and, subsequently, it was reduced at 350° C. in an H$_2$ atmosphere for 3 h prior to the catalytic application thereof. The resulting Pd/Ga/HT-4 material, characterised by chemical analysis and ICP-MS, contained ≈0.74% by weight of Pd and ≈0.48% by weight of Ga.

Example 12

Synthesis of the 0.74% Pd/0.29% Ga/HT-4 Catalyst

It was prepared from the HT-4 material prepared as described in Example 1, wherein the incorporation of Ga (0.4% by weight, theoretical) into the HT-4 material was performed by means of the incipient wetness impregnation method, using, in this case, 0.015 g of Ga(NO$_3$)$_3$.9H$_2$O dissolved in 1.920 g of Milli-Q water, to impregnate 1.000 g of HT-4. Once impregnated, the solid obtained was dried in an oven at 100° C. for 14-16 h. The incorporation of Pd (1.0% by weight, theoretical) into the solid obtained was performed by means of the incipient wetness impregnation method, using, in this case, 0.095 g of Pd(NH$_3$)$_4$Cl$_2$.6H$_2$O dissolved in 1.500 g of Milli-Q water, to impregnate 1.540 g of the solid obtained in the first impregnation. Once impregnated, the final solid was dried in an oven at 100° C. for 14-16 h; thereafter, it was calcined in air at 450° C. for 3-4 h, and, subsequently, it was reduced at 350° C. in an H$_2$ atmosphere for 3 h prior to the catalytic application thereof. The resulting Pd/Ga/HT-4 material, characterised by chemical analysis and ICP-MS, contained ≈0.74% by weight of Pd and ≈0.29% by weight of Ga.

Example 13

Synthesis of the 5.0% Cu-HT-4 Catalyst

This catalyst was synthesised to illustrate hydrotalcite-type catalysts containing Cu, such as those cited in application WO2009026523. Various catalysts were synthesised with different concentrations of Cu, and the catalyst that provided the best results, in terms of selectivity and conversion, was selected in order to be compared to the catalysts of the invention.

It was prepared by means of a standard co-precipitation process using two solutions. The first solution contained 28.73 g of Mg(NO$_3$)$_2$.6H$_2$O, 10.50 g of Al(NO$_3$)$_3$.9H$_2$O and 1.20 g of Cu(NO$_3$)$_2$.3H$_2$O, dissolved in 56.25 g of Milli-Q water, with a molar concentration of (Al+Mg+Cu) of 1.5. The second solution contained 12.72 g of NaOH and 10.25 g of Na$_2$CO$_3$ in 73.71 g of Milli-Q water, and was used to produce the adequate precipitation of the Mg, Al and Cu species, and to set the pH of the total mixture at ≈13. Both solutions were added (total flow velocity=30 ml/h for approximately 4 h) to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 14-16 h. The hydrotalcite (Cu-HT-4) obtained was calcined in air at 450° C. for 3-4 h, to obtain a mixed oxide with a Mg/Al molar ratio ≈3.8, a Cu content of ≈5.0% by weight, characterised by chemical analysis and ICP-MS.

Example 14

Synthesis of the 3.5% Co-HT-4 Catalyst

This catalyst was synthesised to illustrate hydrotalcite-type catalysts containing Co, such as those cited in application US20100160693. Various catalysts were synthesised with different concentrations of Co, and the catalyst that provided the best results, in terms of selectivity and conversion, was selected in order to be compared to the catalysts of the invention.

It was prepared by means of a standard co-precipitation process using two solutions. The first solution contained 28.82 g of Mg(NO$_3$)$_2$.6H$_2$O, 14.05 g of Al(NO$_3$)$_3$.9H$_2$O and 1.17 g of Co(NO$_3$)$_2$.6H$_2$O dissolved in 58.54 g of Milli-Q water, with a molar concentration of (Al+Mg+Cu) of 1.5. The second solution contained 13.81 g of NaOH and 10.87 g of Na$_2$CO$_3$ in 77.91 g of Milli-Q water, and was used to produce the adequate precipitation of the Mg, Al and Cu species, and to set the pH of the total mixture at ≈13. Both solutions were added (total flow velocity=30 ml/h for approximately 4 h) to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 14-16 h. The hydrotalcite (Co-HT-4) obtained was calcined in air at 450° C. for 3-4 h, to obtain a mixed oxide with a Mg/Al molar ratio ≈3.8, a Co content of ≈3.5% by weight, characterised by chemical analysis and ICP-MS.

Example 15

Synthesis of the 2.5% Ni-HT-4 Catalyst

This catalyst was synthesised to illustrate hydrotalcite-type catalysts containing Ni, such as those cited in application US20100160693. Various catalysts were synthesised with different concentrations of Ni, and the catalyst that provided the best results, in terms of selectivity and conversion, was selected in order to be compared to the catalysts of the invention.

It was prepared by means of a standard co-precipitation process using two solutions. The first solution contained 29.71 g of Mg(NO$_3$)$_2$.6H$_2$O, 10.81 g of Al(NO$_3$)$_3$.9H$_2$O and 0.78 g of Ni(NO$_3$)$_2$.6H$_2$O, dissolved in 56.54 g of Milli-Q water, with a molar concentration of (Al+Mg+Cu) of 1.5. The second solution contained 12.85 g of NaOH and 10.37 g of Na$_2$CO$_3$ in 74.33 g of Milli-Q water, and was used to produce the adequate precipitation of the Mg, Al and Ni species, and to set the pH of the total mixture at ≈13. Both solutions were added (total flow velocity=30 ml/h for approximately 4 h) to a container under vigorous stirring at room temperature. The gel formed was aged at room temperature for 1-2 h; thereafter, it was filtered and washed with distilled water until the carbonate was not detected in the filtered liquid (at pH≈7). Subsequently, the solid was dried in an oven at 60° C. for 14-16 h. The hydrotalcite (Ni-HT-4) obtained was calcined in air at 450° C. for 3-4 h, to obtain a mixed oxide with a Mg/Al molar ratio ≈3.8, a Co content of ≈2.5% by weight, characterised by chemical analysis and ICP-MS.

Example 16

Comparative Catalytic Activity of the Catalysts of Examples 1, 2, 5, 7 and 13-15 Under $N_2$ Atmosphere 3500 mg of ethanol and 200 mg of one of the catalytic materials of Examples 1, 2, 5, 7 and 13-15 were introduced into a 12-ml stainless steel autoclave reactor, with a Teflon-coated inside and a magnetic stirrer. The reactor was hermetically closed, and the system contained a connector to a pressure meter (manometer), another connector for the loading of gases and a third outlet which made it possible to take samples at different time intervals. The reactor was initially pressurised with 24 bars of $N_2$, and heated to 200° C. under continuous stirring, until the total system pressure reached approx. 30 bars (reaction time=0). Liquid samples (≈50 µl) were taken at different time intervals until 17-24 hours of reaction. The samples were filtered and diluted in a 2% by weight of chlorobenzene in acetonitrile standard solution, and analysed by means of gas chromatography in a GC-3900 Varian equipped with an FID detector and a 60-m TRB-624 capillary column; the ethanol conversion, in molar percentage (EtOH conv.), was calculated from the composition of the mixture obtained:

(initial moles of reagent−final moles of reagent)/
(initial moles of reagent*100)

The selectivities to n-butanol obtained were also calculated in molar percentage (Select. n-ButOH):

(moles of *n*-butanol/moles of total products)*100

The total yield of n-butanol (Yield n-ButOH) was calculated as:

(EtOH conv.*Select.*n*-ButOH)/100

In this manner, the following results were obtained:

TABLE 1

Catalytic activity of different mixed metal oxides in the transformation of ethanol into n-butanol under nitrogen atmosphere.

| Ex. | Catalyst | T (h) | EtOH conv. | Select. n-ButOH | Yield n-ButOH | TON[a] |
|---|---|---|---|---|---|---|
| 1 | HT-4 | 5 | 3.6 | 50.5 | 1.82 | 1 |
| 2 | 1.00% Pd/HT-4 | 5 | 15.5 | 76.9 | 11.9 | 629 |
| 5 | 0.80% Pt/HT-4 | 5 | 13.0 | 82.0 | 10.7 | 1268 |
| 7 | 1% Pd/0.29% Ga-HT-4 | 5 | 15.8 | 76.5 | 12.1 | 630 |
| 13 | 5.0% Cu-HT-4 | 5 | 8.3 | 68.8 | 5.92 | 42 |
| 14 | 3.5% Co-HT-4 | 5 | 1.2 | 76.2 | 0.91 | 8 |
| 15 | 2.5% Ni-HT-4 | 5 | 2.0 | 65.2 | 1.304 | 19 |

[a]TON = Turn Over Number in (mol/mol Pd or Pt).

These results show that the catalyst impregnated with Pd or Pt give better yields than the catalyst comprising co, Ni or Cu.

Example 17

Comparative Catalytic Activity of the Catalysts of Examples 2-5 and 7-12 Under $N_2$ Atmosphere 3500 mg of ethanol and 200 mg of one of the catalytic materials of Examples 2-5 to 7-12 were introduced into a 12-ml stainless steel autoclave reactor, with a Teflon-coated inside and a magnetic stirrer. The reactor was hermetically closed, and the system contained a connector to a pressure meter (manometer), another connector for the loading of gases and a third outlet which made it possible to take samples at different time intervals. The reactor was initially pressurised with 24 bars of $N_2$, and heated to 200° C. under continuous stirring, until the total system pressure reaches approx. 30 bars (reaction time=0). Liquid samples (≈50 µl) were taken at different time intervals until 17-24 hours of reaction. The samples were filtered and diluted in a 2% by weight of chlorobenzene in acetonitrile standard solution, and analysed by means of gas chromatography in a GC-3900 Varian equipped with an FID detector and a 60-m TRB-624 capillary column; the ethanol conversion, in molar percentage (EtOH conv.), was calculated from the composition of the mixture obtained:

(initial moles of reagent−final moles of reagent)/
(initial moles of reagent*100)

The selectivities to n-butanol obtained were also calculated in molar percentage (Select. n-ButOH):

(moles of *n*-butanol/moles of total products)*100

The total yield of n-butanol (Yield n-ButOH) was calculated as:

(EtOH conv.*Select.*n*-ButOH)/100

In this manner, the following results were obtained:

TABLE 2

Catalytic activity of different mixed metal oxides in the transformation of ethanol into n-butanol under nitrogen atmosphere.

| Ex. | Catalyst | T (h) | EtOH conv. | Select. n-ButOH | Yield n-ButOH | TON[a] |
|---|---|---|---|---|---|---|
| 2 | 1% Pd/HT-4 | 5 | 15.5 | 76.9 | 11.9 | 629 |
|  |  | 17 | 17.2 | 75.8 | 13.0 | 695 |
| 3 | 0.5% Pd/HT-4 | 5 | 14.1 | 82.5 | 11.7 | 1145 |
|  |  | 17 | 16.8 | 80.6 | 13.5 | 1359 |
| 4 | 0.25% Pd/HT-4 | 5 | 10.2 | 79.0 | 8.1 | 2073 |
|  |  | 17 | 12.2 | 77.5 | 9.4 | 2460 |
| 5 | 0.80% Pt/HT-4 | 5 | 13.0 | 82.0 | 10.7 | 1268 |
|  |  | 17 | 14.2 | 50.5 | 7.2 | 1385 |
| 7 | 1% Pd/0.29% Ga-HT-4 | 5 | 15.8 | 76.5 | 12.1 | 630 |
|  |  | 17 | 20.4 | 75.5 | 15.4 | 825 |
| 8 | 0.5% Pd/0.29% Ga-HT-4 | 5 | 14.8 | 79.3 | 11.7 | 1195 |
|  |  | 17 | 17.7 | 78.6 | 13.9 | 1435 |
| 9 | 0.24% Pd/0.29% Ga-HT-4 | 5 | 12.5 | 76.4 | 9.6 | 2539 |
|  |  | 17 | 16.0 | 74.8 | 12.0 | 3237 |
| 10 | 1.06% Pt/0.29% Ga-HT-4 | 5 | 12.0 | 69.0 | 8.3 | 881 |
|  |  | 17 | 13.8 | 56.6 | 7.8 | 1013 |
| 11 | 0.74% Pd/0.48% Ga-HT-4 | 5 | 14.5 | 65.0 | 9.4 | 829 |
|  |  | 17 | 18.1 | 62.1 | 11.2 | 1034 |
| 12 | 0.74% Pd/0.29% Ga/HT-4 | 5 | 13.0 | 63.0 | 8.2 | 743 |
|  |  | 17 | 16.3 | 60.0 | 9.8 | 931 |

[a]TON = Turn Over Number in (mol/mol Pd or Pt).

These results show that, at a given concentration of palladium, the hydrotalcite-derived catalysts that comprise gallium in their structure provide higher yields of n-butanol under nitrogen atmosphere than their analogues without gallium. Moreover, they also show a higher TON than the catalysts possessing the same concentration of Pd but without gallium in their structure. This fact is an indication of the greater stability of the catalysts of the invention under the reaction conditions.

Moreover, as can be observed in FIG. 1, the catalysts of the invention show higher selectivities to butanol under $N_2$ atmosphere at a given ethanol conversion value than the catalysts in the state of the art.

Another fact worth mentioning is that the catalysts of the invention make it possible to achieve lower concentrations of Pd whilst maintaining high yields of n-butanol, as compared to the catalysts in the state of the art.

Example 18

Comparative Catalytic Activity of the Catalysts of Examples 2-5 and 7-12 Under $N_2$—$H_2$ Atmosphere 3500 mg of ethanol and 200 mg of one of the catalytic materials of Examples 2-5 and 7-12 were introduced into a 12-ml stainless steel autoclave reactor, with a Teflon-coated inside and a magnetic stirrer. The reactor was hermetically closed, and the system contained a connector to a pressure meter (manometer), another connector for the loading of gases and a third outlet which made it possible to take samples at different time intervals. The reactor was initially pressurised with 10 bars of hydrogen, and, thereafter, was taken to a total pressure of 24 bars by adding $N_2$. Subsequently, it was heated to 200° C. under constant stirring, until the total system pressure reaches approx. 32-33 bars (reaction time=0). Liquid samples (≈50 μl) were taken at different time intervals until 17-24 hours of reaction. The samples were filtered and diluted in a 2% (W/W) of chlorobenzene in acetonitrile standard solution, and analysed by means of gas chromatography in a GC-3900 Varian equipped with an FID detector and a 60-m TRB-624 capillary column; the ethanol conversion, in molar percentage (EtOH conv.), was calculated from the composition of the mixture obtained:

(initial moles of reagent–final moles of reagent)/
(initial moles of reagent*100)

The selectivities to n-butanol obtained were also calculated in molar percentage (Select. n-ButOH):

(moles of *n*-butanol/moles of total products)*100

The total yield of n-butanol (Yield n-ButOH) was calculated as:

(EtOH conv.*Select.*n*-ButOH)/100

In this manner, the following results were obtained:

TABLE 3

Catalytic activity of different mixed metal oxides in the transformation of ethanol into n-butanol under nitrogen and hydrogen atmosphere.

| Ex. Catalyst | T (h) | EtOH conv. | Select. n-ButOH | Yield n-ButOH | TON[a] |
|---|---|---|---|---|---|
| 2  1% Pd/HT-4 | 5 | 12.1 | 95.8 | 11.6 | 488 |
|  | 17 | 13.8 | 83.2 | 11.5 | 560 |
| 3  0.5% Pd/HT-4 | 5 | 10.5 | 93.0 | 9.8 | 849 |
|  | 17 | 12.5 | 93.3 | 11.7 | 1015 |
| 4  0.25% Pd/HT-4 | 5 | 7.8 | 96.0 | 7.5 | 1585 |
|  | 17 | 10.0 | 96.0 | 9.6 | 2025 |
| 5  0.80% Pt/HT-4 | 5 | 5.0 | 87.0 | 4.4 | 488 |
|  | 17 | 8.0 | 85.0 | 6.8 | 780 |
| 7  1% Pd/0.29% Ga-HT-4 | 5 | 11.7 | 90.9 | 10.6 | 472 |
|  | 17 | 15.1 | 92.8 | 14.0 | 612 |
| 8  0.5% Pd/0.29% Ga-HT-4 | 5 | 11.6 | 94.0 | 10.9 | 937 |
|  | 17 | 14.1 | 92.0 | 13.0 | 1141 |
| 9  0.24% Pd/0.29% Ga-HT-4 | 5 | 10.1 | 94.0 | 9.4 | 2034 |
|  | 17 | 14.3 | 93.0 | 13.3 | 2888 |
| 10  1.06% Pt/0.29% Ga-HT-4 | 5 | 8 | 96.0 | 7.7 | 587 |
|  | 17 | 10.4 | 95.0 | 9.9 | 763 |
| 11  0.74% Pd/0.48% Ga-HT-4 | 5 | 7.0 | 85.0 | 6.0 | 400 |
|  | 17 | 9.7 | 85.1 | 8.3 | 554 |
| 12  0.74% Pd/0.29% Ga-HT-4 | 5 | 6.0 | 87.0 | 5.2 | 343 |
|  | 17 | 10.8 | 87.6 | 9.5 | 617 |

[a]TON = Turn Over Number in (mol/mol Pd or Pt).

These results show that, at a given concentration of palladium, the hydrotalcite-derived catalysts that comprise gallium in their structure provide higher yields of n-butanol under nitrogen and hydrogen atmosphere than their analogues without gallium. Moreover, they also show a higher TON than the catalysts possessing the same concentration of Pd but without gallium in their structure. This fact is an indication of the greater stability of the catalysts of the invention under the reaction conditions. On the other hand, it is worth noting that incorporating hydrogen into the reaction mixture increases the selectivities to butanol.

Figure 2:
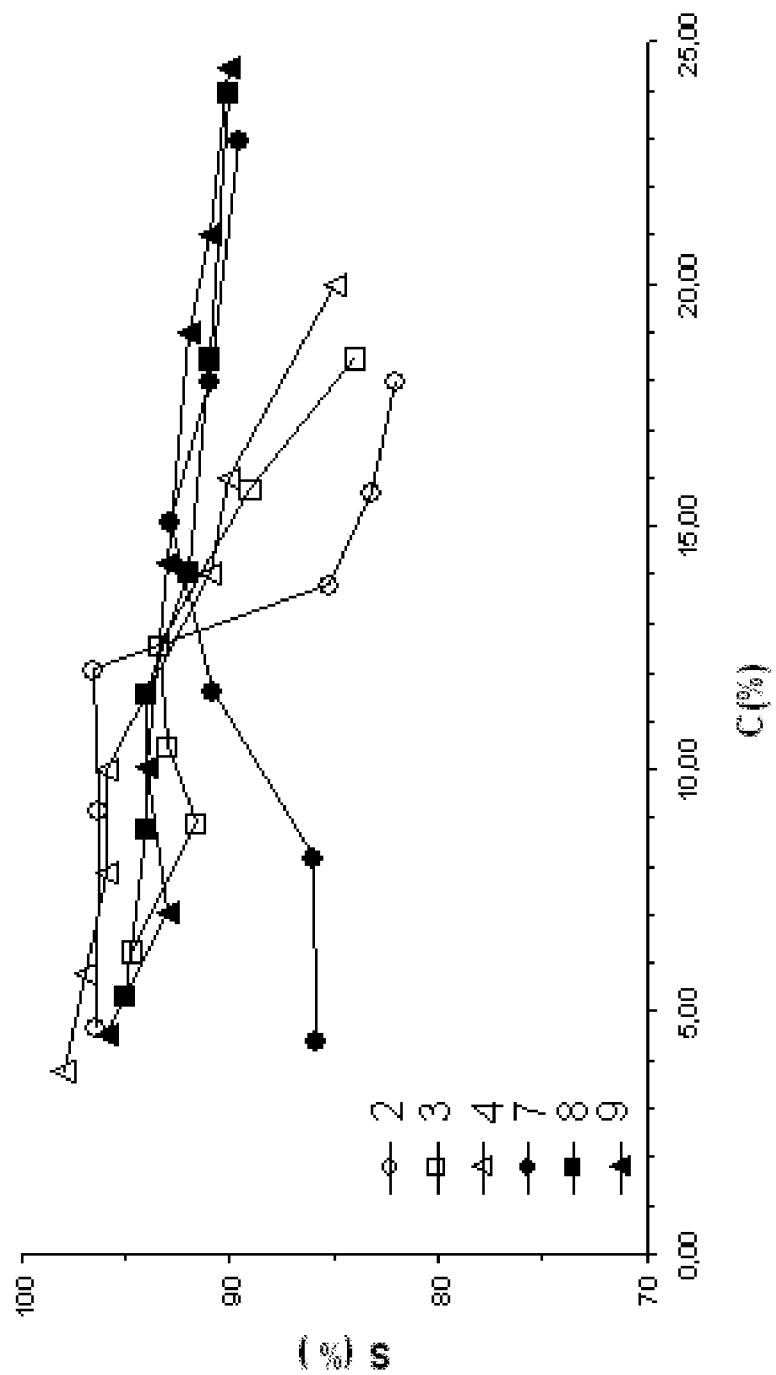
FIG. 2. Shows a comparative graph of the selectivities of the Pd/HT-4 and Pd/Ga-HT-4 catalysts in an $N_2$—$H_2$ atmosphere as a function of the conversion. Legend same as in FIG. 1.
Figure 3:
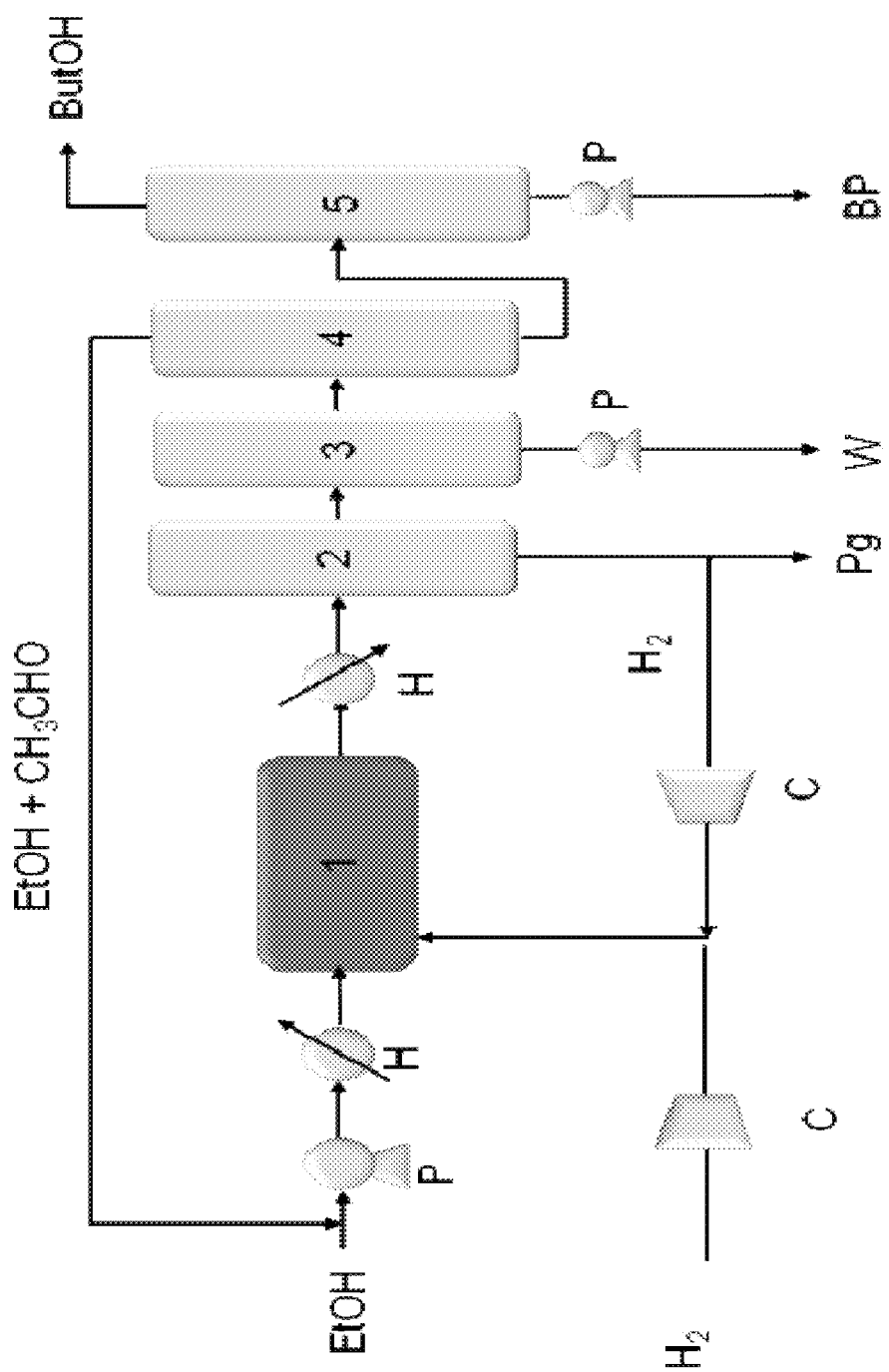
FIG. 3. Shows the process diagram for the obtaining of butanol from ethanol with recirculation of unreacted ethanol and acetaldehyde, P: Pump; H: heat exchanger; EtOH: ethanol; EtOH+$CH_3CHO$: recirculation of ethanol and acetaldehyde; C: compressor; ButOH: butanol; Pg: purge; W: water; BP: other by-products; 1: Catalytic condensation reactor; 2: gas/liquid separation; 3: Dehydration; 4: Ethanol column; 5: butanol refining.

Moreover, as can be observed in FIG. 2, the catalysts of the invention show higher selectivities to butanol in an $N_2$—$H_2$ atmosphere at a given ethanol conversion value than the catalysts in the state of the art.

Another fact worth mentioning is that the catalysts of the invention make it possible to achieve lower concentrations of Pd whilst maintaining high yields of n-butanol, as compared to the catalysts in the state of the art.

Example 19

Effect of Co-Feeding the Intermediate Acetaldehyde to the Contact Step Between the Reagents and the Catalyst of the Invention In a 33-cm long and 0.83-cm diameter stainless steel fixed bed reactor, a constant flow of the reagents described in Table 4 and 50 ml/min of $N_2$ were fed to the reactor with a catalyst mass load of 3300 mg of the catalytic material described in example 7. The reactor was then connected to the synthesis loop, which contained a connector to a pressure meter (manometer), another connector for the reagents input and a third one for the outlet. Operating pressure at the reactor was controlled by a valve sited at the outlet stream. Once achieved operating temperature, the inlet stream was fed to the reactor synthesis loop. Once the composition of the outlet stream was stable during time, its composition was analysed through gas chromatography in a GC-Agilent 6890N equipped with a FID and TCD detector, a capillary column Rt-U PLOT of 30 m and two packed columns in series (PORAPPACK QS, 3.6-m long, and CARBOXEN 1000, 4.5-m long). Once the composition of the outlet stream was known, ethanol conversion in molar percentage (EtOH conv.) as well as for acetaldehyde conversion ($CH_3CHO$ conv.) were obtained from the following equation:

(initial moles of reactive–final moles of reactive)/
(initial moles of reactive*100), Liquid Hourly Space Velocity (LHSV) is calculated as:

(L/*h* EtOH)/L catalyst

The selectivities to n-butanol obtained were also calculated in molar percentage (Select. n-ButOH):

(moles of *n*-butanol/moles of total products)*100

Productivity of n-butanol (Prod. ButOH (g/kg·h)) was calculated as:

(Grammes of *n*-butanol produced)/(kg of catalyst*hours of reaction)

The total yield of n-butanol (Yield n-ButOH) was calculated as:

(EtOH conv.*Select. *n*-ButOH)/100

Table 4 shows the conversion and the production of butanol from ethanol without feeding acetaldyde (7NA and 7NB) or feeding a 1% wt of acetaldehyde in the feeding stream (7RA and 7RB) at two different operating conditions (A: T=226° C., $H_2$/EtOH=0.95; B: T=238° C., $H_2$/EtOH=0.68). All the reactions were carried out under 75 bar and at a liquid hourly space velocity (LHSV) of 1.4 $h^{-1}$.

TABLE 4

Effect of the co-feeding of acetaldehyde in the obtaining of butanol from ethanol.

| | T (° C.) | $H_2$/ EtOH | EtOH conv. | $CH_3CHO$ conv | Select. n-ButOH | Prod. ButOH (g/kg · h) | Yield n-ButOH |
|---|---|---|---|---|---|---|---|
| 7NA | 226 | 0.95 | 4.55 | — | 75.37 | 37.33 | 3.43 |
| 7RA | 226 | 0.95 | 4.98 | 75.12 | 83.07 | 42.44 | 4.14 |
| 7NB | 238 | 0.68 | 9.58 | — | 74.82 | 73.66 | 7.17 |
| 7RB | 238 | 0.68 | 9.96 | 59.82 | 81.02 | 83.13 | 8.07 |

T: temperature of the reaction;
$H_2$/EtOH: ratio hydrogen/ethanol in the feed;
Conv. EtOH (%): conversion of ethanol in %;
Conv. $CH_3CHO$ (%): conversion of acetaldehyde;

This example shows that the co-feeding acetaldehyde increases the conversion and selectivity of $C_3$-$C_{15}$ higher alcohols.

The invention claimed is:

1. A process for obtaining $C_3$-$C_{15}$ higher alcohols which comprises a contact step between at least one reagent selected from the group consisting of methanol, ethanol, propanol and isopropanol, and a catalyst, where said catalyst is a metal oxide that comprises the following metals:
   M1 is at least one bivalent metal selected from the group consisting of Mg, Zn, Cu, Co, Mn, Fe, Ni and Ca, and M2 is trivalent Ga,
   and further contains a noble metal selected from the group consisting of Pd, Pt, Ru, Rh and Re.

2. The process according to claim 1, wherein the metal oxide further comprises an M3 metal, where M3 is at least one trivalent metal selected from the group consisting of Al, La, Fe, Cr, Mn, Co and Ni.

3. The process according to claim 2, wherein the metal oxide is obtained from the total or partial thermal decomposition of a hydrotalcite with the formula $[M1_{1-(x+y)}M2_yM3_x(OH)_2][A^{m-}_{(x+y)/m} \cdot nH_2O]$, where:
   A is at least one anion selected from the group consisting of hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), and
   x is a value between 0 and 0.5; y is a value between 0.00001 and 0.49; m is an integer between 1 and 4; and n is greater than 0.

4. The process according to claim 3, wherein the hydrotalcite is obtained by the co-precipitation of M1, M2 and M3 compounds.

5. The process according to claim 4, wherein the co-precipitation is performed by the addition of a solution of at least one compound selected from the group consisting of carbonate, bicarbonate and hydroxide to a solution of M1, M2 and M3 compounds.

6. The process according to claim 3, wherein the thermal decomposition of hydrotalcite is performed by means of calcination under atmosphere of oxygen, nitrogen or any mixture thereof at a temperature ranging between 250° C. and 650° C.

7. The process according to claim 1, wherein M1 is Mg.

8. The process according to claim 3, wherein M3 is Al.

9. The process according to claim 3, wherein A is at least one anion selected from the group consisting of $CO_3^{2-}$, $HCO_3^-$, $O_2^-$ and $OH^-$.

10. The process according to claim 1, wherein the noble metal is added to the metal oxide by wet impregnation, incipient volume impregnation or deposition-precipitation.

11. The process according to claim 10, wherein, following the addition of the noble metal, there is a calcination step and a reduction step subsequent to said calcination.

12. The process according to claim 1, wherein the higher alcohol is n-butanol.

13. The process according to claim 1, wherein the reagent is ethanol, methanol or any mixture thereof.

14. The process according to claim 1, wherein the contact between the reagent and the catalyst is performed at a pressure of up to 120 bar.

15. The process according to claim 1, wherein the contact between the reagent and the catalyst is performed under atmosphere of nitrogen, argon, hydrogen or any mixture thereof.

16. The process according to claim 1, further comprising a step of separation of unreacted reagents from the obtained $C_3$-$C_{15}$ higher alcohols.

17. The process according to claim 16, wherein the unreacted reagents are recirculated to the contact step between reagents and catalyst.

18. The process according to claim 16, wherein the unreacted reagent comprises ethanol.

19. The process according to claim 1, further comprising a step of separation of intermediates from the obtained $C_3$-$C_{15}$ higher alcohols.

20. The process according to claim 19, wherein the intermediates are recirculated to the contact step between reagents and catalyst.

21. The process according to claim 19, wherein the intermediate comprises an aldehyde.

22. The process according to claim 1, further comprising the feeding of fresh acetaldehyde to the contact step between reagents and catalyst.

23. The process according to claim 22, wherein the acetaldehyde is obtained from the dehydration of ethanol.

* * * * *